United States Patent
Glass et al.

(10) Patent No.: US 7,120,485 B2
(45) Date of Patent: Oct. 10, 2006

(54) METHOD AND SYSTEM FOR DETECTION OF CARDIAC ARRHYTHMIA

(75) Inventors: Leon Glass, Montreal (CA); Katsumi Tateno, Kitakyushu (JP)

(73) Assignee: Medtronic, Inc., Minneapolis, MN (US)

( * ) Notice: Subject to any disclaimer, the term of this patent is extended or adjusted under 35 U.S.C. 154(b) by 363 days.

(21) Appl. No.: 10/380,919

(22) PCT Filed: Sep. 20, 2001

(86) PCT No.: PCT/CA01/01360

§ 371 (c)(1),
(2), (4) Date: Sep. 17, 2003

(87) PCT Pub. No.: WO02/24068

PCT Pub. Date: Mar. 28, 2002

(65) Prior Publication Data

US 2005/0165320 A1    Jul. 28, 2005

Related U.S. Application Data

(60) Provisional application No. 60/234,198, filed on Sep. 20, 2000.

(51) Int. Cl.
*A61B 5/04*    (2006.01)

(52) U.S. Cl. .................................. 600/515; 600/521
(58) Field of Classification Search ............... 600/515; 607/14, 25; 128/920, 923
See application file for complete search history.

(56) References Cited

U.S. PATENT DOCUMENTS

| | | | | | |
|---|---|---|---|---|---|
| 4,328,552 | A | * | 5/1982 | Stovall | 702/111 |
| 4,417,306 | A | * | 11/1983 | Citron et al. | 600/521 |
| 4,974,598 | A | * | 12/1990 | John | 600/509 |
| 5,330,508 | A | * | 7/1994 | Gunderson | 607/14 |
| 5,509,425 | A | * | 4/1996 | Feng | 600/515 |
| 5,603,331 | A | * | 2/1997 | Heemels et al. | 600/508 |

* cited by examiner

Primary Examiner—Robert E. Pezzuto
Assistant Examiner—Eric D. Bertram
(74) Attorney, Agent, or Firm—Paul H. McDowall; Michael C. Soldner; Girma Wolde-Michael

(57) ABSTRACT

There are many different serious cardiac arrhythmias. The present invention uses measurements of RR intervals (inter-beat intervals) to detect, in particular but not exclusively, atrial fibrillation of a patient. Atrial fibrilation is a serious ailment in which the heartbeat is generally rapid and irregular. Probability density histograms of ΔRRs (difference between two successive RR intervals) collected during atrial fibrillation of a plurality of subjects are used as a template for the detection of atrial fibrillation. In one implementation, there are 16 standard probability density ΔRRs histograms every 50 ms of mean RR interval of a certain number of beats, where the mean RR interval ranges from 350 ms to 1149 ms. Similarity between the standard probability density histograms and a test density probability histogram of ΔRRs of a patient is estimated by the Kolmogorov-Smirnov test. If the test density histogram is not significantly different from the standard density histogram, atrial fibrillation is detected.

16 Claims, 16 Drawing Sheets

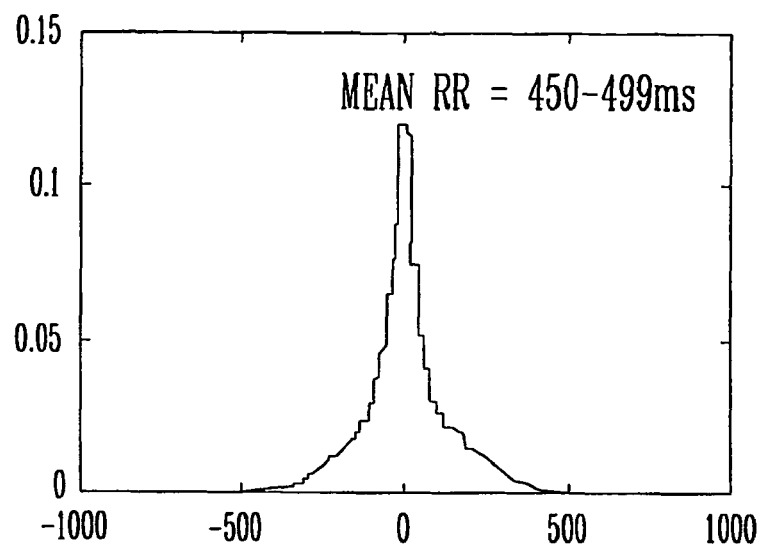
FIG_3c
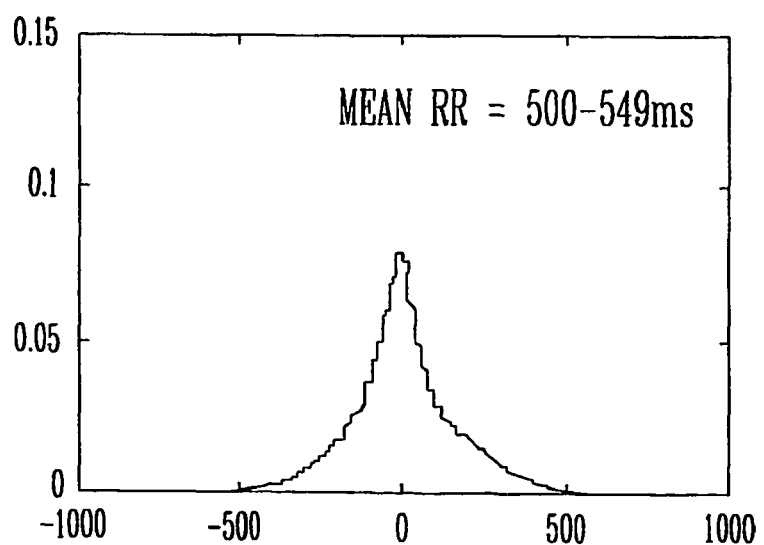
FIG_3d

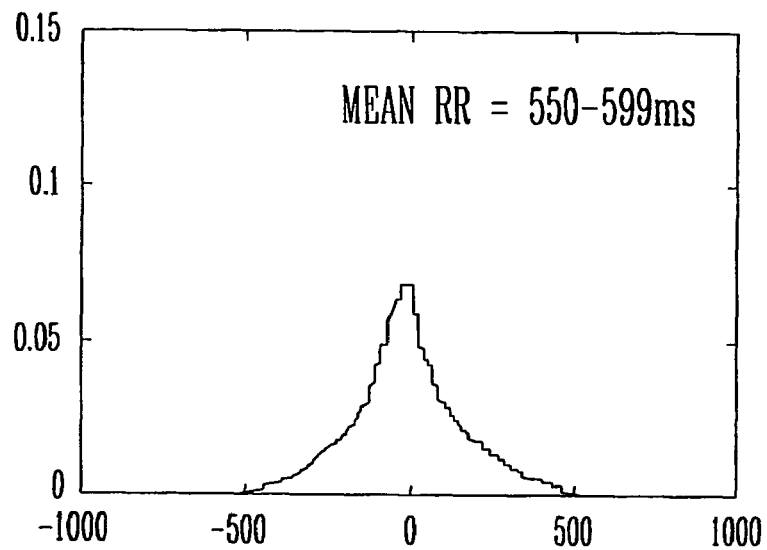
FIG_3E
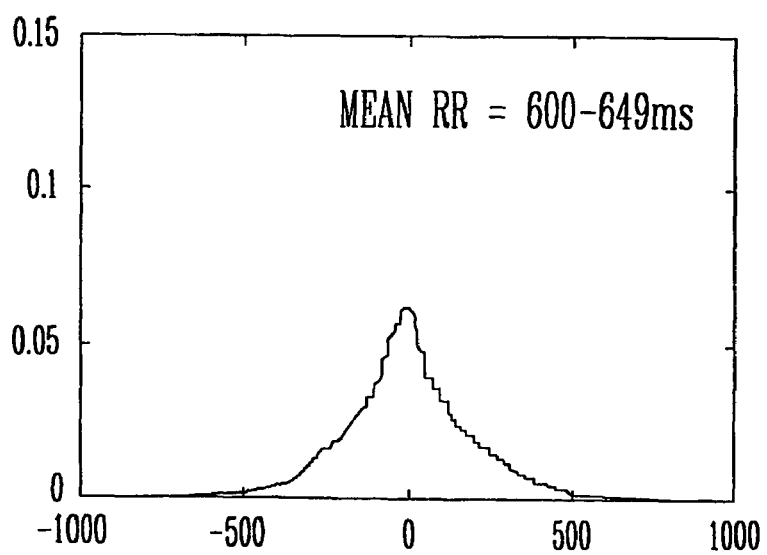
FIG_3F

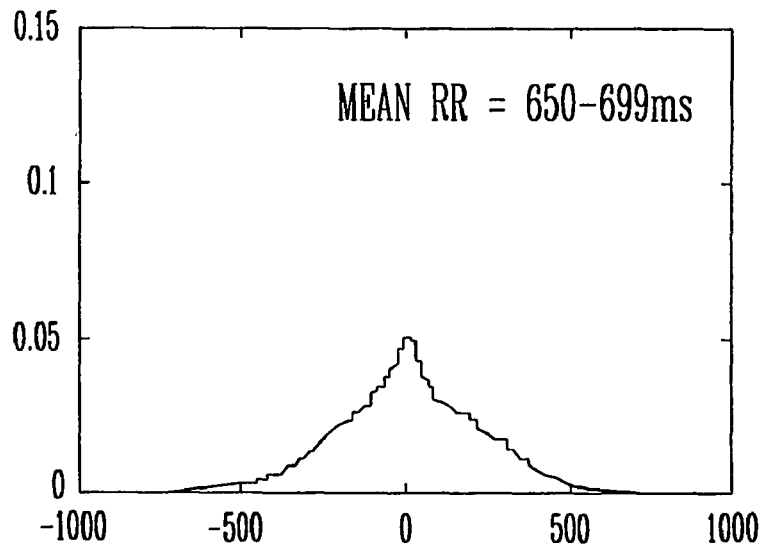
FIG_3g
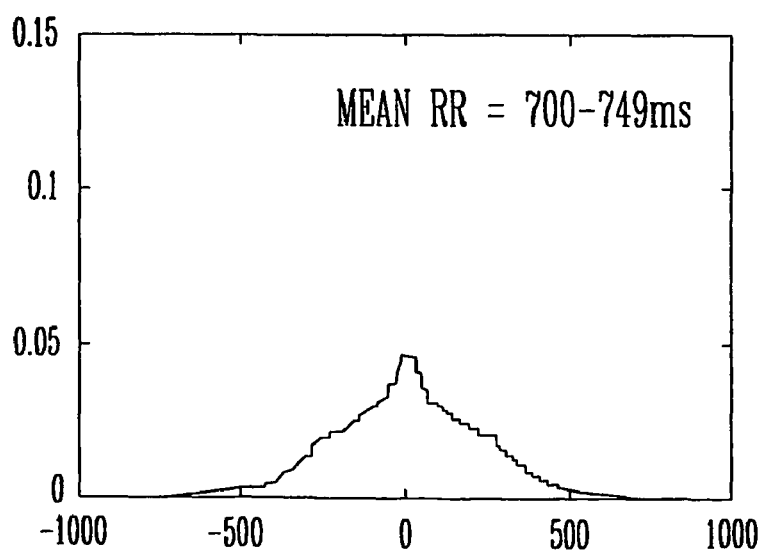
FIG_3h

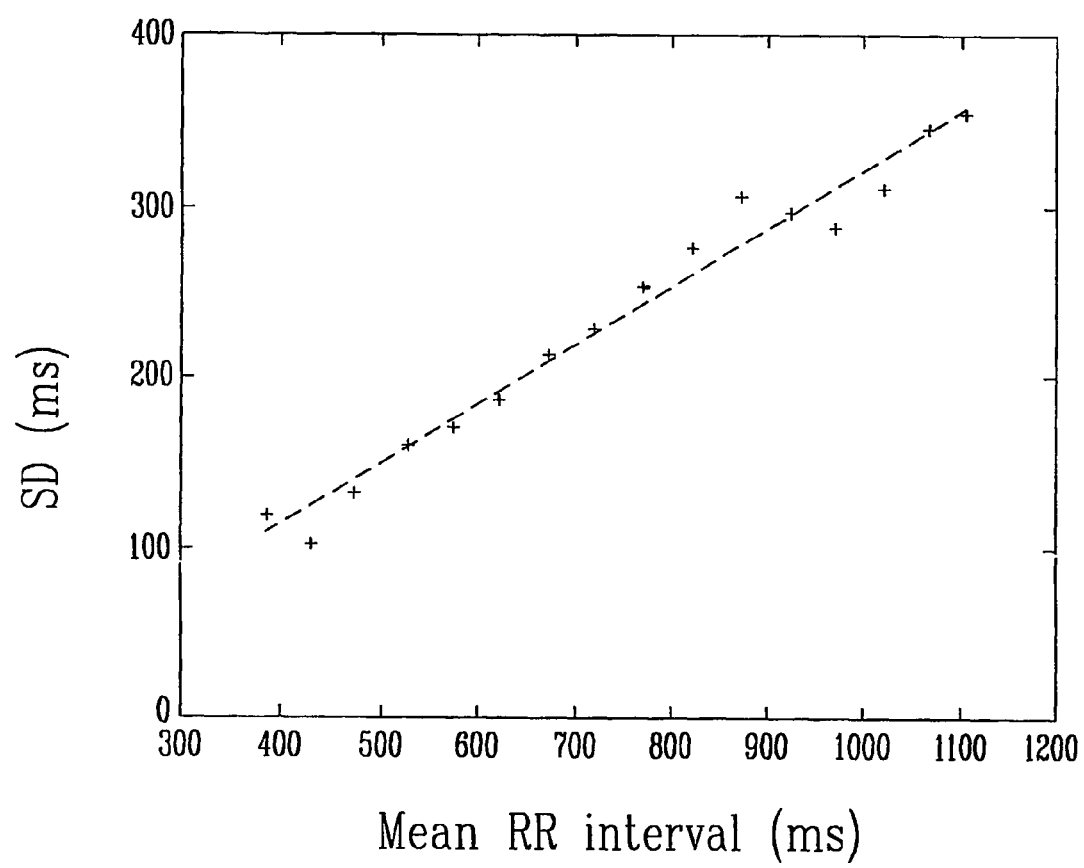
FIG_4

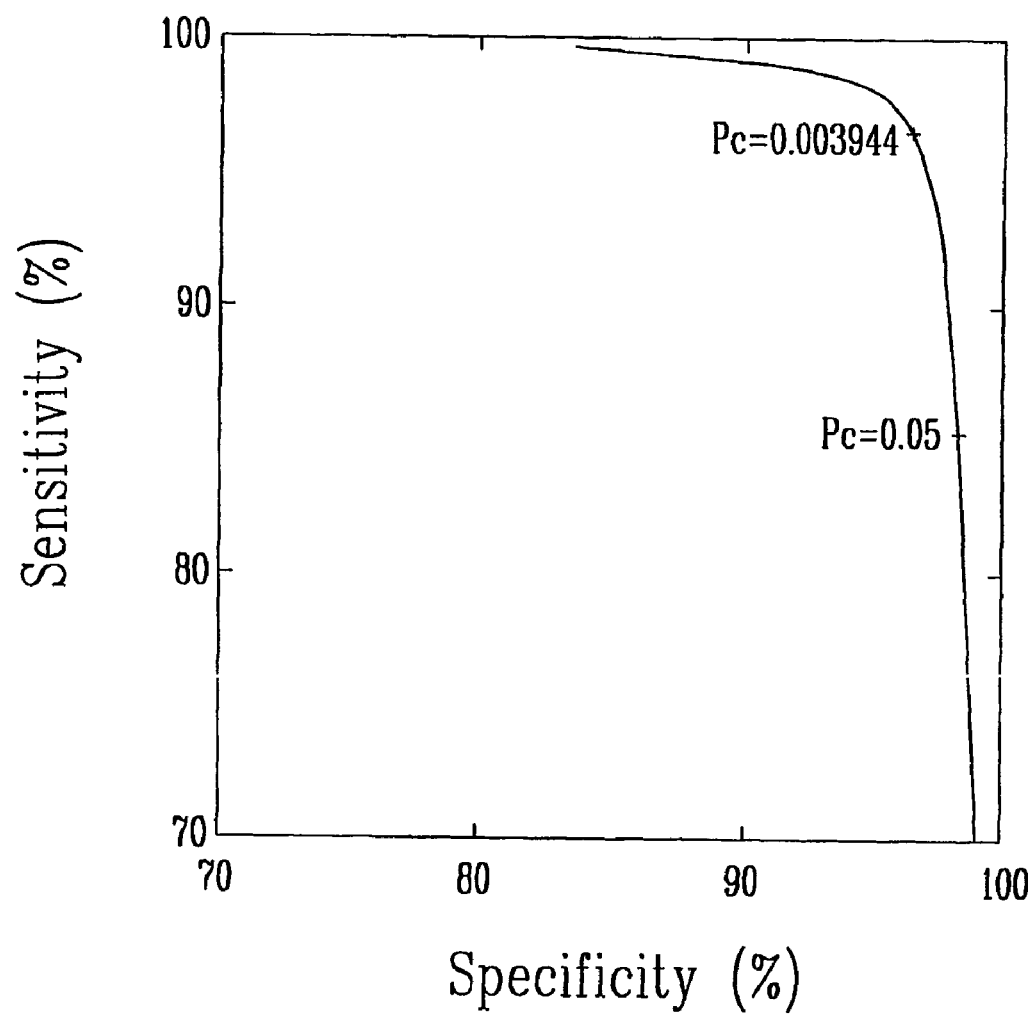
FIG_7

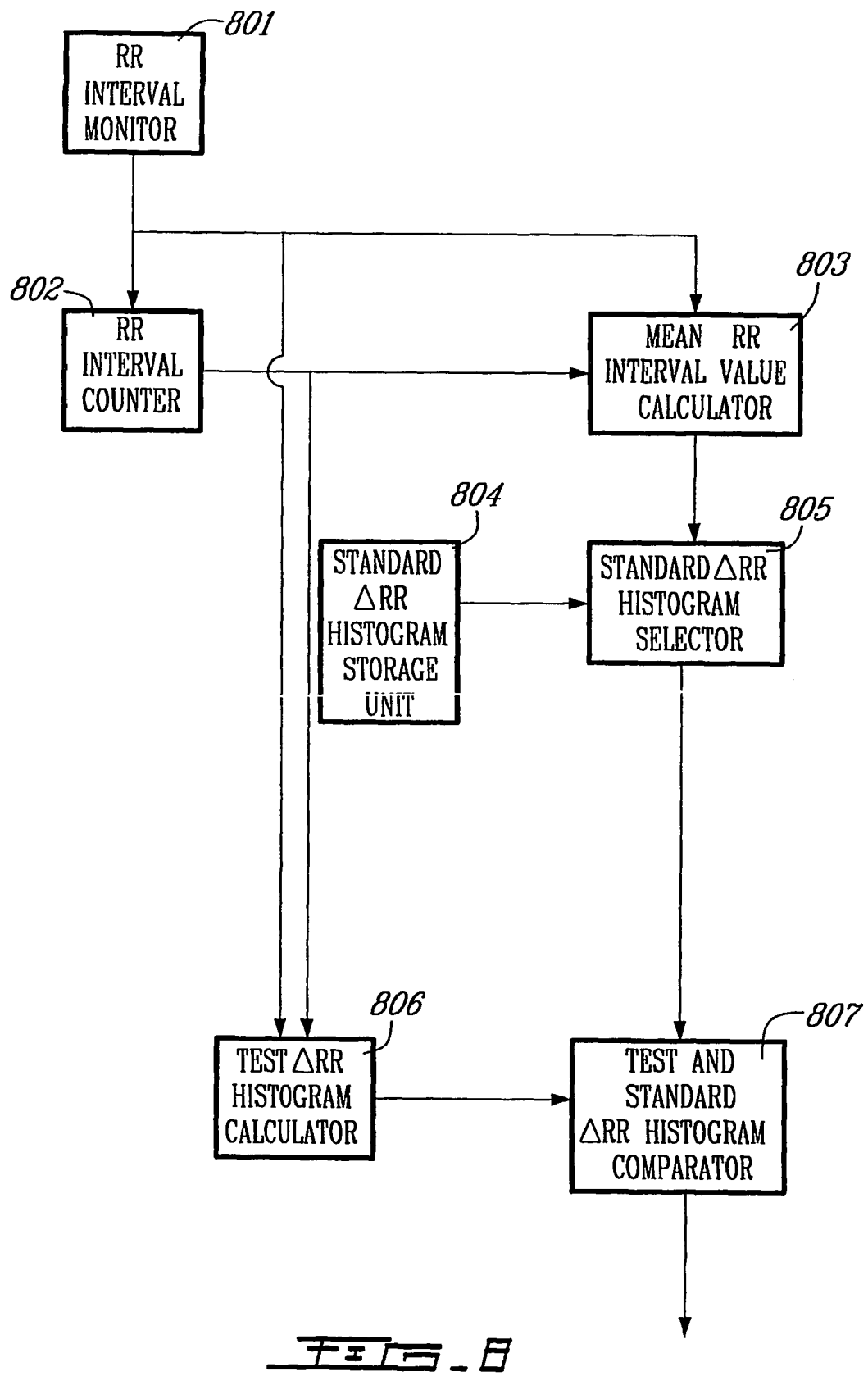
FIG_8

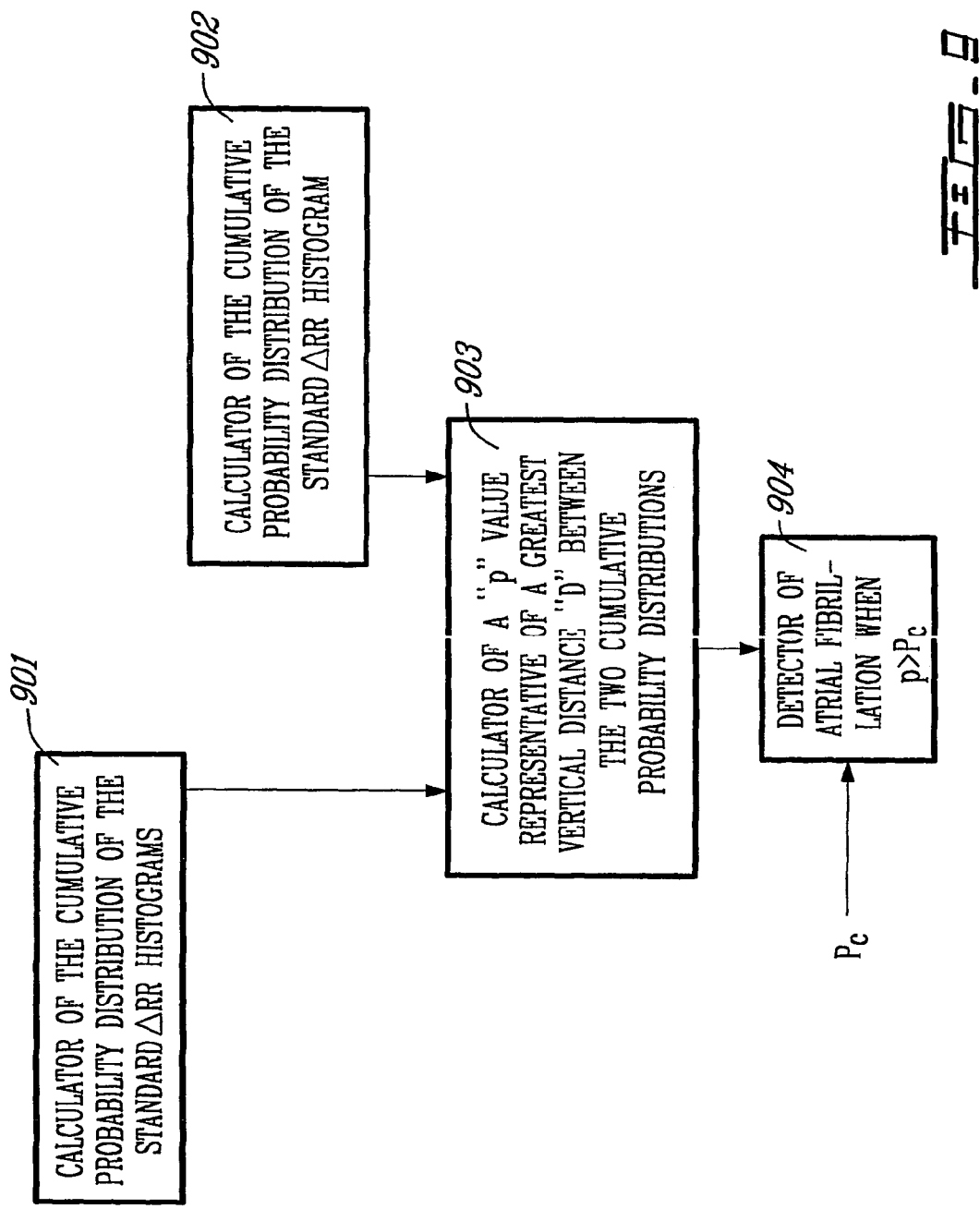

METHOD AND SYSTEM FOR DETECTION OF CARDIAC ARRHYTHMIA

This application is a 35 U.S.C. § 371 national filing of International Application No. PCT/CA01/01360, filed Sep. 20, 2001, which claims the benefit of U.S. Provisional Application No. 60/234,198, filed Sep. 20, 2000.

BACKGROUND OF THE INVENTION

1. Field of the Invention

The present invention relates to a method and a system for detecting cardiac arrhythmias from internally and/or externally detected activity of the heart.

2. Brief Description of the Prior Art

Atrial fibrillation is a serious and common cardiac arrhythmia. Atrial fibrillation is associated with rapid, irregular atrial activation with life threatening sequelae such as stroke. The atrial activations are irregularly transmitted through the atrioventricular node leading to a correspondingly irregular sequence of ventricular activations as monitored by the ventricular interbeat (RR) intervals on the surface electrocardiogram (ECG). An RR interval is an interval between two successive heart beats. Clinically, in the surface ECG, atrial fibrillation is diagnosed by absence of P waves (normally associated with the near synchronous activation of the atria) and a rapid irregular ventricular rate. P waves are difficult to determine automatically and irregular baseline activity of the ECG is common in atrial fibrillation.

Although a number of different methods have been proposed to test for atrial fibrillation based on knowledge of the RR intervals and/or the surface ECG, the detection of atrial fibrillation based on this data nevertheless poses substantial problems (Murgatroyd, et al. "Identification of Atrial Fibrillation Episodes in Ambulatory Electrocardiographic Recordings: Validation of a Method for Obtaining Labeled R—R Interval Files," Pacing and Clinical Electrophysiology, (1995), pp. 1315–1320). In the following description, the main strategies that have been proposed to assess atrial fibrillation based on knowledge of the RR intervals and/or ECG will be briefly reviewed.

Since RR intervals during atrial fibrillation have a larger standard deviation and a more rapid decay of the autocorrelation function, there are proposals that the standard deviation and the autocorrelation function can be used to distinguish atrial fibrillation from sinus rhythm (Bootsma, et al. "Analysis of RR Intervals in Patients with Atrial Fibrillation at Rest and During Exercise," Circulation, (1970), pp. 783–794). Since other abnormal rhythms also have a large standard deviation of RR intervals and a rapid decay of the autocorrelation function, these methods are difficult to apply in concrete situations.

Moody and Mark (G. Moody, et al. "A New Method for Detecting Atrial Fibrillation Using R—R Intervals," Computers in Cardiology, (1983), pp. 227–230) classify RR intervals as short, long or regular. They then construct a Markov model for the probabilities for transitions between RR intervals in each of the three different length classes. Atrial fibrillation data has typical transition probabilities not shared by normal rhythms or other arrhythmia. Although the Markov model has high sensitivity for detecting atrial fibrillation, it tends to have a relatively low predictive value of a positive test.

Pinciroli and Castelli have investigated the morphology of histograms of RR intervals collected during atrial fibrillation and other arrhythmia (F. Pinciroli, et al. "Pre-clinical Experimentation of a Quantitative Synthesis of the Local Variability in the Original R—R Interval Sequence in the Presence of Arrhythmia," Automedica, (1986), vol.6, pp. 295–317. Pinciroli and Castelli, 1986). They demonstrated that the histograms of the ratio between successive RR intervals show characteristic differences between normal rhythm and atrial fibrillation. The histogram of the ratio between successive RR intervals is symmetrical to the mean value. No quantitative methods were proposed to quantify the symmetry or to use it to develop a quantitative test.

Since the baseline of the ECG is irregular during atrial fibrillation, Slocum (J. Slocum, et al. "Computer Detection of Atrial Fibrillation on the Surface Electrocardiogram," Computers in Cardiolody, (1987), pp. 253–254) has proposed that the regularity of the baseline, as determined by the power spectrum of the residual ECG after subtraction of the baseline of the QRS complexes can be used to detect atrial fibrillation. This method is necessarily sensitive to small amounts of noise that might corrupt the baseline of the ECG.

Implantable ventricular and atrial defibrillators are devices that distinguish atrial and ventricular fibrillation from other rhythms. Typically, electrodes in these devices record intracardiac activity directly from the atria and ventricles. The methods that are used to detect atrial fibrillation in these devices cannot be easily applied to recordings that give information about the timing of the QRS complexes (U.S. Pat. No. 6,144,878, issued to Schroeppel on Nov. 7, 2000, U.S. Pat. No. 6,035,233 issued to Schroeppel on Mar. 7, 2000, U.S. Pat. No. 5,749,900 issued to Schroeppel on May 24, 1998, U.S. Pat. No. 6,064,906 issued to Langberg et al. on May 16, 2000, U.S. Pat. No. 5,772,604 issued to Langberg et al. on Jun. 30, 1998, U.S. Pat. No. 6,061,592 issued to Nigam on May 9, 2000, U.S. Pat. No. 5,951,592 issued to Murphy on Sep. 14, 1999, U.S. Pat. No. 5,941,831 issued to Turcoft on Aug. 24, 1999, U.S. Pat. No. 5,591,215 issued to Greenhut et al. on Jan. 7, 1997).

Analysis of a histogram of the interbeat intervals can be used to discriminate between ventricular fibrillation and ventricular tachycardia. By counting the number of beats in predetermined interval classes, an algorithm identifies a given sequence as ventricular fibrillation or ventricular tachycardia (U.S. Pat. No. 5,330,508 issued to Gunderson on Jul. 19, 1994). While this patent suggests that the invention is of value in detecting and treating atrial fibrillation (column 2, lines 29–31), it does not provide specific embodiment for detecting and treating atrial fibrillation.

Based on the foregoing review of the prior art, it is apparent that there is a need to develop a method and a system for determining whether or not a given recording is atrial fibrillation based on the timing of the QRS complexes as measured from an internal and/or external monitor. Assessment of whether a patient is in atrial fibrillation based on the timing of the QRS complexes would be extremely useful, for example, for assessing the efficacy of specific drugs on a patient fitted with a monitoring device that measures the timing of the QRS complexes.

SUMMARY OF THE INVENTION

In accordance with the present invention there is provided a method for detecting cardiac arrhythmia of a patient, comprising detecting RR intervals of the patient wherein each RR interval is an interval between two heart beats, constructing standard histograms of $\Delta RR$s collected during cardiac arrhythmia of a plurality of subjects wherein each $\Delta RR$ is a difference between two successive RR intervals, constructing test histograms of ΔRRs of the patient from the detected RR intervals of this patient, and comparing the standard and test histograms to detect whether the patient suffers from cardiac arrhythmia.

In accordance with preferred embodiments:

the standard and test histograms are probability density histograms, a mean value of a given number of successive RR intervals of the patient is calculated, and a standard probability density histogram is chosen in relation to this mean value;

the comparison of the standard and test histograms comprises adjusting a specificity-altering and sensitivity-altering parameter;

the comparison of the standard and test histograms comprises:

calculating a standard cumulative probability distribution from the standard ΔRR probability density histograms;

calculating a test cumulative probability distribution from the test ΔRR probability density histograms;

computing a deviation between these standard and test distributions; and detecting cardiac arrhythmia when the computed deviation is higher than the specificity-altering and sensitivity-altering parameter.

The present invention also relates to a system for detecting cardiac arrhythmia of a patient, comprising:

an RR interval detecting monitor detecting RR intervals of the patient, wherein each RR interval is an interval between two heart beat;

a standard ΔRR histogram storage unit in which are stored standard histograms of ΔRRs collected during cardiac arrhythmia of a plurality of subjects, wherein each ΔRR is a difference between two successive RR intervals;

a test ΔRR histogram calculator supplied with the detected RR intervals from the monitor and constructing test histograms of the ΔRRs of the patient; and a standard and test ΔRR histograms comparator supplied with the standard and test histograms, this comparator comprising a detector of cardiac arrhythmia of the patient responsive to the comparison of the standard and test histograms.

It is within the scope of the present invention to apply the above concept to detection of not only atrial fibrillation but also to other cardiac arrhythmias including in particular but not exclusively atrial flutter, multifocal atrial tachycardia, ventricular tachycardia, premature ventricular contractions, etc., as well as to detection of other body phenomenon involving electrical activity. It is also within the scope of the present invention to use signals other than the RR intervals, histograms other than ΔRR probability density histograms, tests other than the KS test, and series of ΔRRs other than 100, and that other methods besides the Komogorov-Smirnov test can be used to compare test histograms with the standard histograms.

The foregoing and other objects, advantages and features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 4 is the standard deviation of ΔRR which consists of the standard ΔRR probability density histogram as a function of mean RR interval.

FIG. 7 shows the receiver operating characteristic curve (ROC) when this method is tested on the MIT-BIH atrial fibrillation/flutter database. The specificity increases with increase in $P_c$, while the sensitivity decreases with an increase in $P_c$.

FIG. 8 is a block diagram of a preferred embodiment of the system according to the present invention for implementing the method of FIG. 2, for detecting atrial fibrillation based on RR intervals.

FIG. 9 is a block diagram of a preferred embodiment of a test and standard ΔRR histogram comparator forming part of the system of FIG. 8.

DETAILED DESCRIPTION OF THE PREFERRED EMBODIMENT

Although the preferred embodiment of the present invention will be described in relation to atrial fibrillation, the same concept can be applied to detection of other cardiac arrhythmias including in particular but not exclusively atrial flutter, multifocal atrial tachycardia, ventricular tachycardia, premature ventricular contractions, etc. This concept can also be applied to detection of other body phenomenon involving electrical activity.

Data was obtained from the MIT-BIH atrial fibrillation/flutter database. The data contains 300 atrial fibrillation episodes, sampled at 250 Hz for 10 hours from Holter tapes of 25 subjects. Arrhythmia detection was carried out by trained observers and was confirmed by an independent evaluation.

Figure 1:
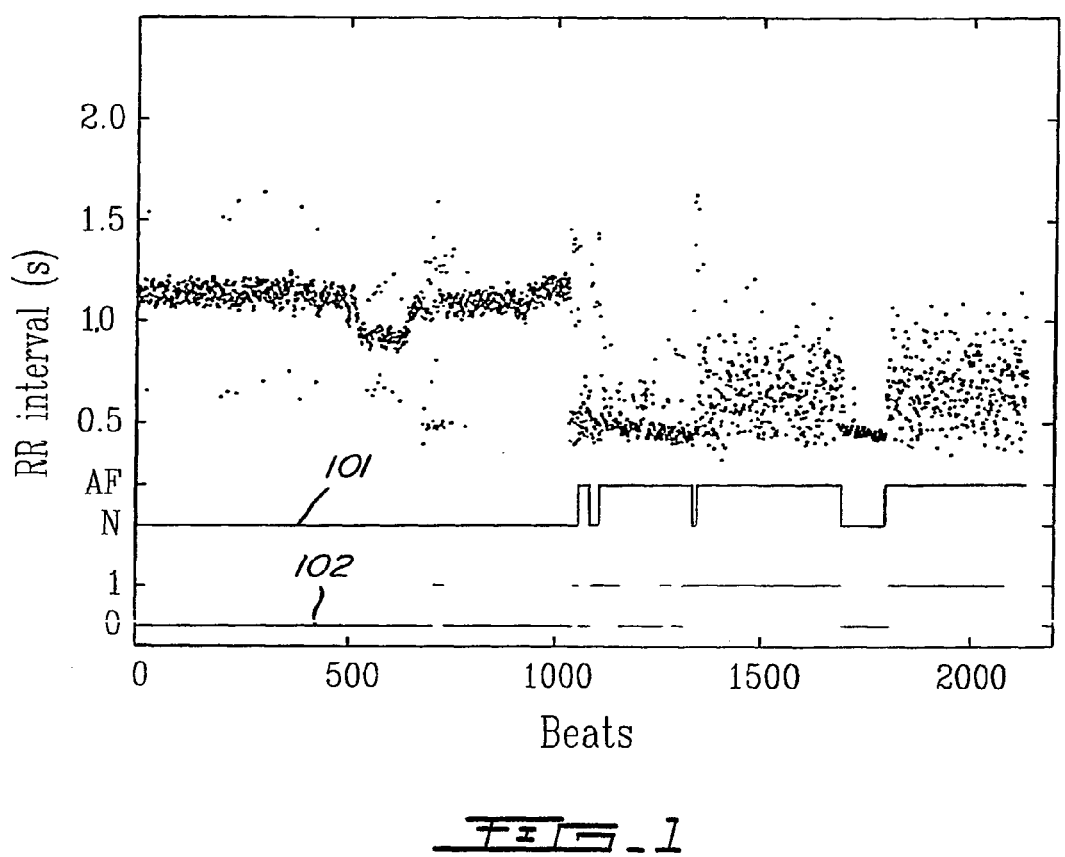
FIG. 1 are time series showing the RR intervals from subject 202 from the MIT-BIH arrhythmia database. The solid line directly under the time series of RR intervals shows the assessment of atrial fibrillation (indicated by AF) or non-atrial fibrillation (indicated by N) as reported in the database. The solid line at the bottom of FIG. 1 indicates the assessment of atrial fibrillation, indicated by 1, and non-atrial fibrillation, indicated by 0, based on an algorithm presented herein.

FIG. 1 is a typical time series of RR intervals from a patient with atrial fibrillation. Immediately under the recording is a solid marker line 101. When atrial fibrillation occurs this marker line 101 is set to AF; otherwise it is set to N, which indicates a rhythm that is not atrial fibrillation. The graph of FIG. 1 also shows a lower solid line 102 indicating the assessment of atrial fibrilation, indicated by 1, and non-atrial fibrillation, indicated by 0, based on an algorithm according to the present invention. At the onset of atrial fibrillation, the rhythm dramatically changes to irregular with large fluctuation. In paroxysmal atrial fibrillation there is sudden starting and stopping of atrial fibrillation.

Figure 2:
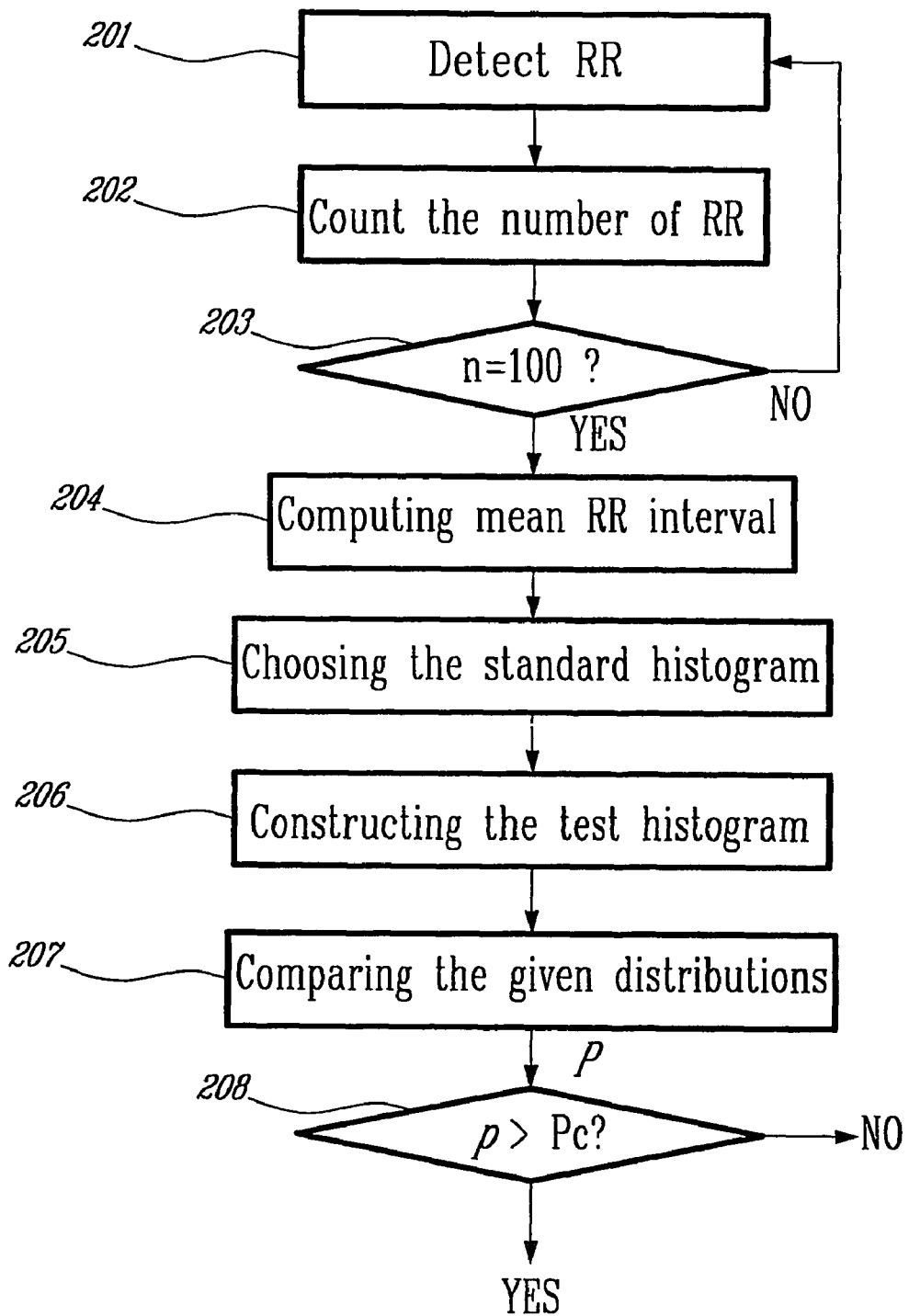
FIG. 2 is a flow chart illustrating a preferred embodiment of the method according to the present invention, for detecting atrial fibrillation based on RR intervals.

FIG. 2 shows a flow chart of a preferred embodiment of the method according to the invention for detecting atrial fibrillation. FIG. 8 is a block diagram of a preferred embodiment of the system according to the invention for implementing this method.

The standard ΔRR probability density histograms are prepared as described hereinafter before the detection of atrial fibrillation, and then stored in an adequate storage unit 804 (FIG. 8).

RR intervals of the patient are first detected (201 of FIG. 2) through an internal and/or external RR interval monitor 801 (FIG. 8) detecting electrical activity of the heart beat of the patient.

ΔRR is defined as the difference between two successive RR intervals. In the preferred embodiment, blocks of 100 successive RR intervals are processed during atrial fibrillation. For that purpose, the detected RR intervals from the monitor 801 are counted (202 of FIG. 2) by a RR interval counter 802 (FIG. 8) until the number of detected RR intervals reaches 100 intervals (203 of FIG. 2).

Figure 3A:
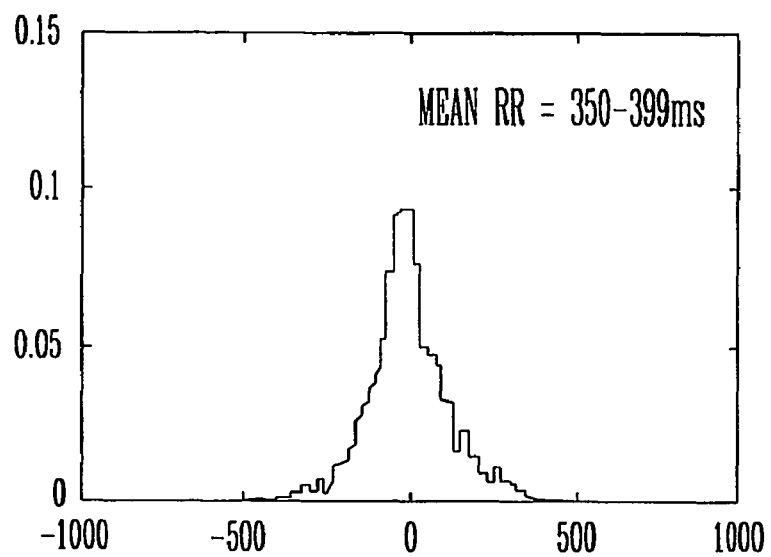
FIGS. 3a–3p are ΔRR standard probability density histograms during atrial fibrillation. Mean RR intervals are a) 350–399 ms, b) 400–449 ms, c) 450–499 ms, d) 500–549 ms, e) 550–599 ms, f) 600–649 ms, g) 650–699 ms, h) 700–749 ms, i) 750–799 ms, j) 800–849 ms, k) 850–899 ms, l) 900–949 ms, m) 950–999 ms, n) 1000–1049 ms, o) 1050–1099 ms, and p) 1100–1049 ms.
Figure 3B:
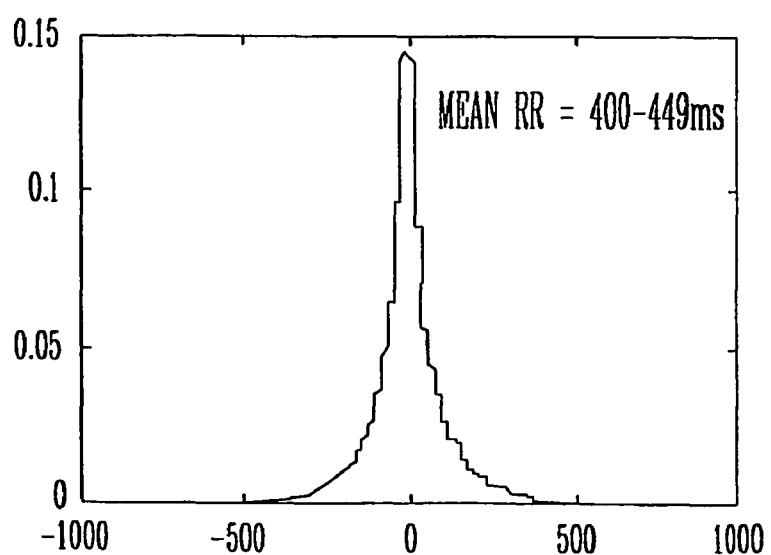
Figure 3I:
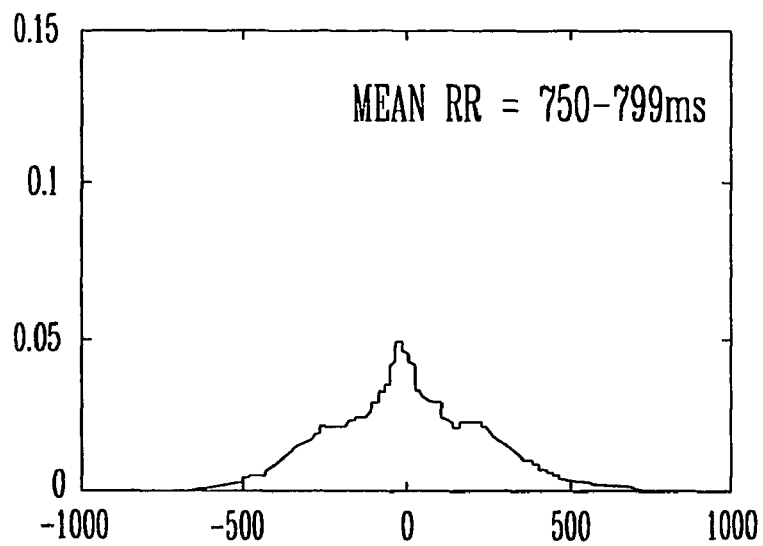
Figure 3J:
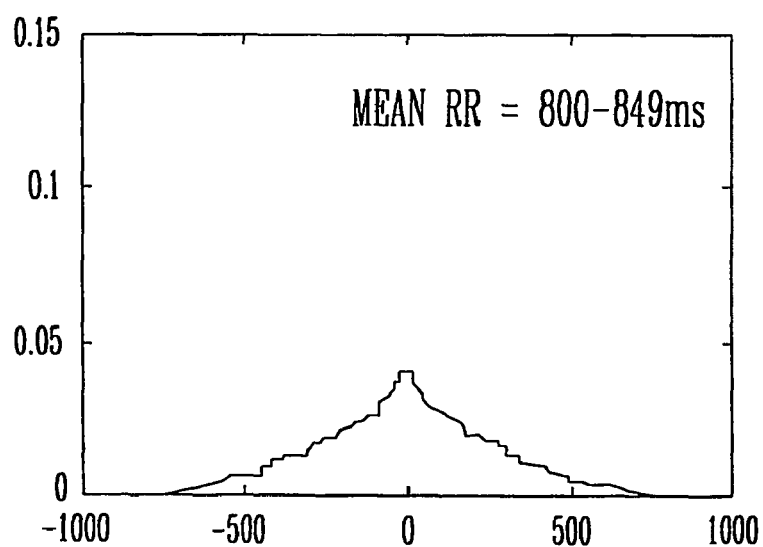
Figure 3K:
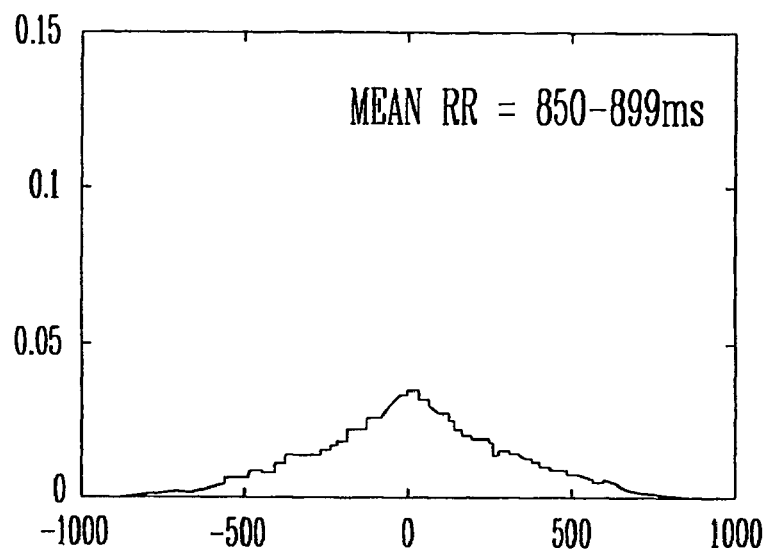
Figure 3L:
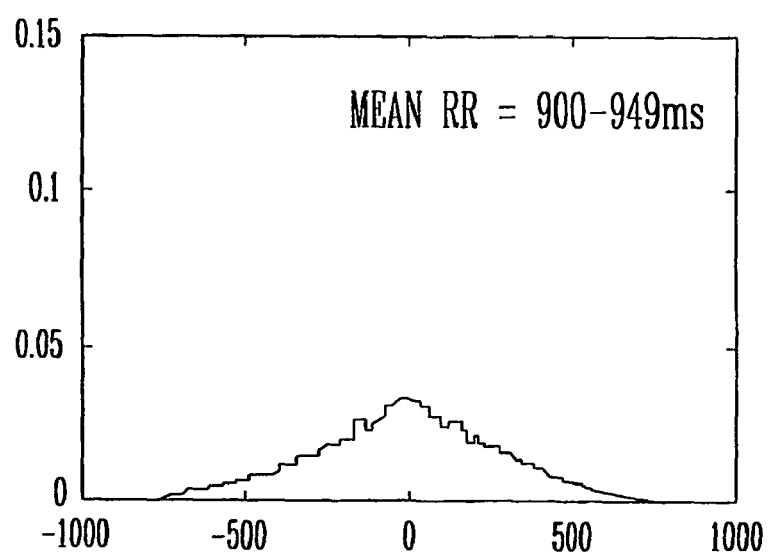
Figure 3M:
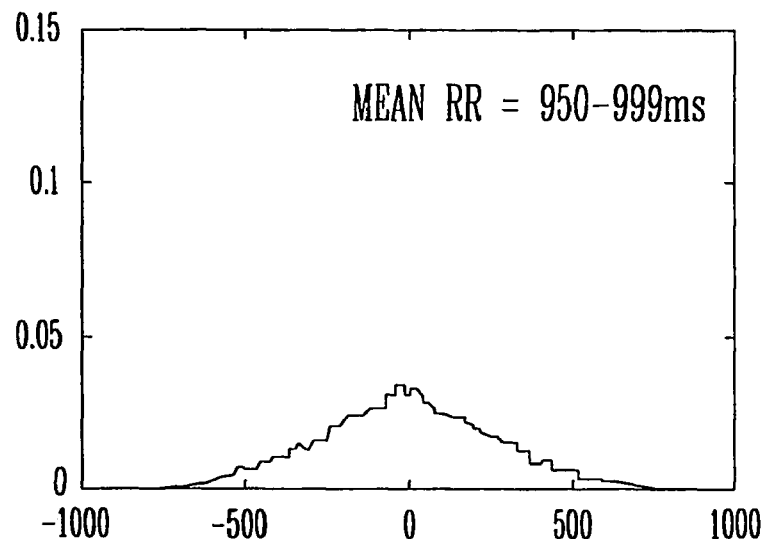
Figure 3N:
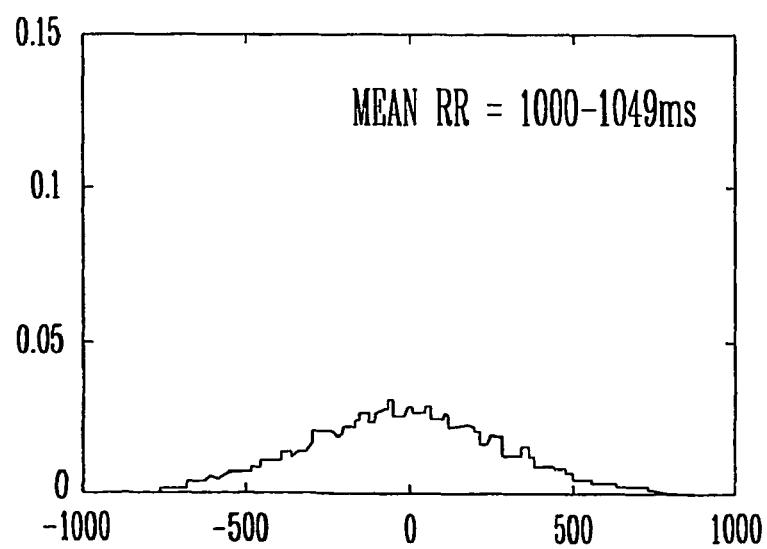
Figure 3O:
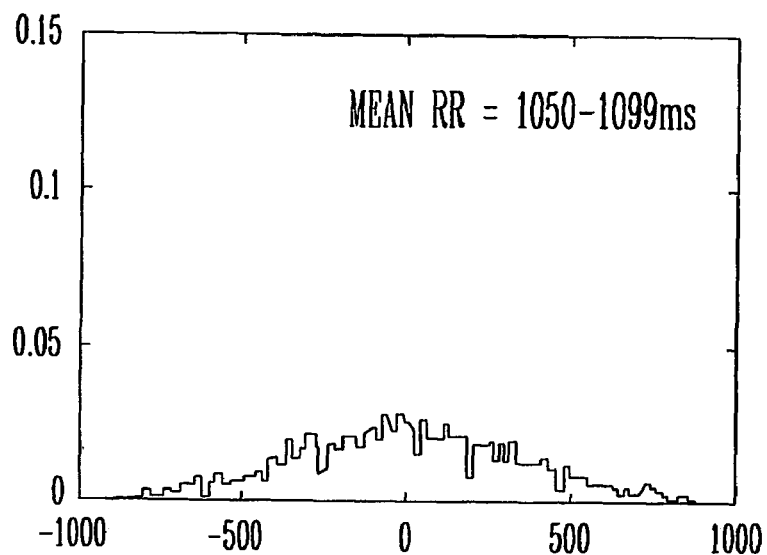
Figure 3P:
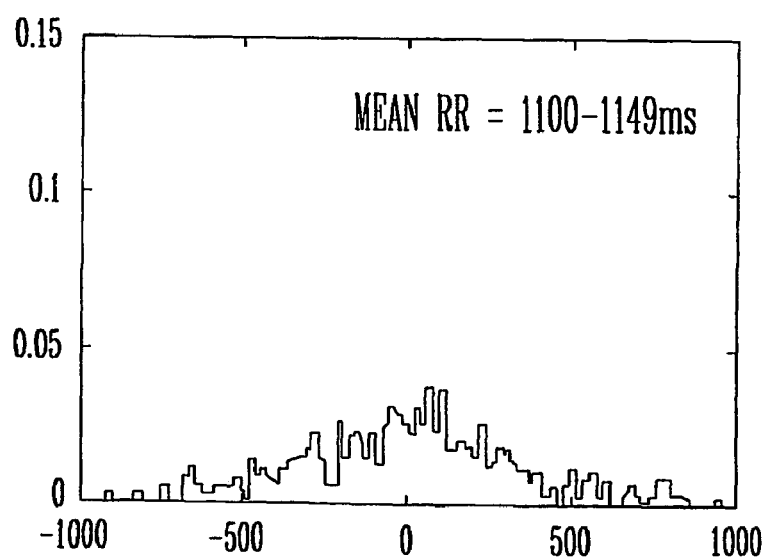

The mean value of each block of 100 RR intervals is computed (204 of FIG. 2) by means of a calculator 803 from the RR intervals from the monitor 801. Of course, the calculator 803 is supplied with the count from the counter 802. This mean value identifies the block of 100 RR intervals as falling into one of sixteen (16) different classes, respectively corresponding to mean values of RR between 350–399 ms, 400–449 ms, 450–499 ms, 500–549 ms, 550–599 ms, 600–649 ms, 650–699 ms, 700–749 ms, 750–799 ms, 800–849 ms, 850–899 ms, 900–949 ms, 950–999 ms, 1000–1049 ms, 1050–1099 ms, and 1100–1049 ms. For each of the sixteen (16) classes, a standard ΔRR probability density histogram is compiled by lumping data together from all the subjects, for example the subjects of the above mentioned MIT-BIH atrial fibrilation/flutter database. The resulting histograms (see for example in FIGS. 3a–3p) are taken to be the standard ΔRR probability density histograms for atrial fibrillation, sorted by the mean RR interval (see for example in FIGS. 3a–3p) and stored in storage unit 804. In other words, a standard ΔRR histogram selector 805 chooses the standard ΔRR probability density histogram (FIGS. 3a–3p) corresponding to the class in which the computed mean value of RR intervals (from 204 in FIG. 2) of the block of 100 RR intervals under consideration falls (205 of FIG. 2).

Obviously, it is within the scope of the present invention to construct the standard ΔRR probability density histograms using a different number of consecutive RR intervals, for example 25, 50 or any other number of consecutive RR intervals. It is also within the scope of the present invention to construct the standard ΔRR probability density histograms using mean RR intervals that lie in other ranges, for example 300–399 ms, 400–499 ms, 500–599 ms, etc.

FIG. 4 shows the standard deviation (SD) of the standard probability density histograms of ΔRR.

Test ΔRR probability density histograms are constructed (206 of FIG. 2) by a calculator 806 from the data obtained from the patient (test record) through the monitor 801. As indicated in the foregoing description, the blocks of 100 successive RR intervals are determined by the counter 802. In order to test for atrial fibrillation in a test record, the test ΔRR probability density histograms based on the blocks of 100 successive RR intervals from the test record, are compared (207 and 208) through a comparator 807 to the chosen standard ΔRR probability density histograms from selector 805.

Figure 5:
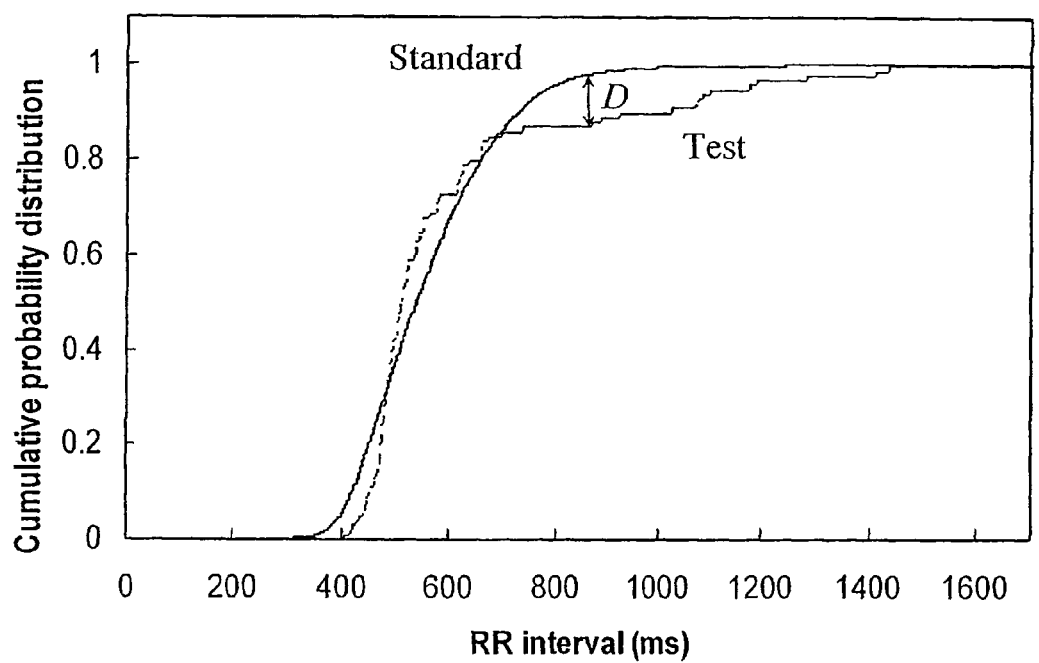
FIG. 5 illustrates the Kolmogorov-Smirnov (KS) test. A cumulative probability distribution based on patient test data is compared with a standard cumulative probability distribution. D is the greatest distance between two cumulative probability distributions.

In the test ΔRR histogram calculator 806 a sequence of 100 RR intervals is centered on each beat in turn, and the relevant test ΔRR probability density histograms are calculated. Also, a standard cumulative probability distribution is calculated by integrating the area under the curves of the standard ΔRR probability density histograms, and a test cumulative probability distribution is computed by integrating the area under the curves of the test ΔRR probability density histograms (FIG. 5).

The similarities between the test histograms for a given patient and the standard histograms are evaluated in the test and standard ΔRR histogram comparator 807 using the above mentioned Kolmogorov-Smirnov (KS) test (207 and 208 of FIG. 2). As indicated, FIG. 5 shows an example of cumulative probability distributions of standard histograms (standard curve) and test histograms (test curve).

Referring to FIG. 9, a calculator 901 (FIG. 9) computes the cumulative probability distribution of the standard probability density ΔRR histograms. A calculator 902 computes the cumulative probability distribution of test probability density ΔRR histograms. According to the KS test, one assesses if two given distributions are different from each other. In other words, the greatest vertical distance D between the two cumulative probability distributions is measured by a calculator 903 which returns a p value in the following manner:

$$p \equiv Q(\lambda) = 2\sum_{j=1}^{\infty}(-1)^{j-1}e^{-2j^2\lambda^2}$$

where $\lambda=(\sqrt{N_e}+0.12+0.11/\sqrt{N_e})*D$.

$$N_e = \frac{N_1 N_2}{N_1 + N_2}.$$

$N_1$ is the number of data points on the standard cumulative probability distribution. $N_2$ is the number of data points in the test cumulative probability distribution. A detector 904 determines whether the p value is greater than a certain, appropriately selected threshold $P_c$, and detection of $p>P_c$ indicates that the cumulative probability distributions are not significantly different from one another. Since the standard ΔRR probability density histograms is representative of atrial fibrillation, a value of $p>P_c$ constitutes a positive identification of atrial fibrillation (or more accurately failure to reject the hypothesis that the test cumulative probability distribution is not atrial fibrillation) (208 in FIG. 2).

Figure 6A:
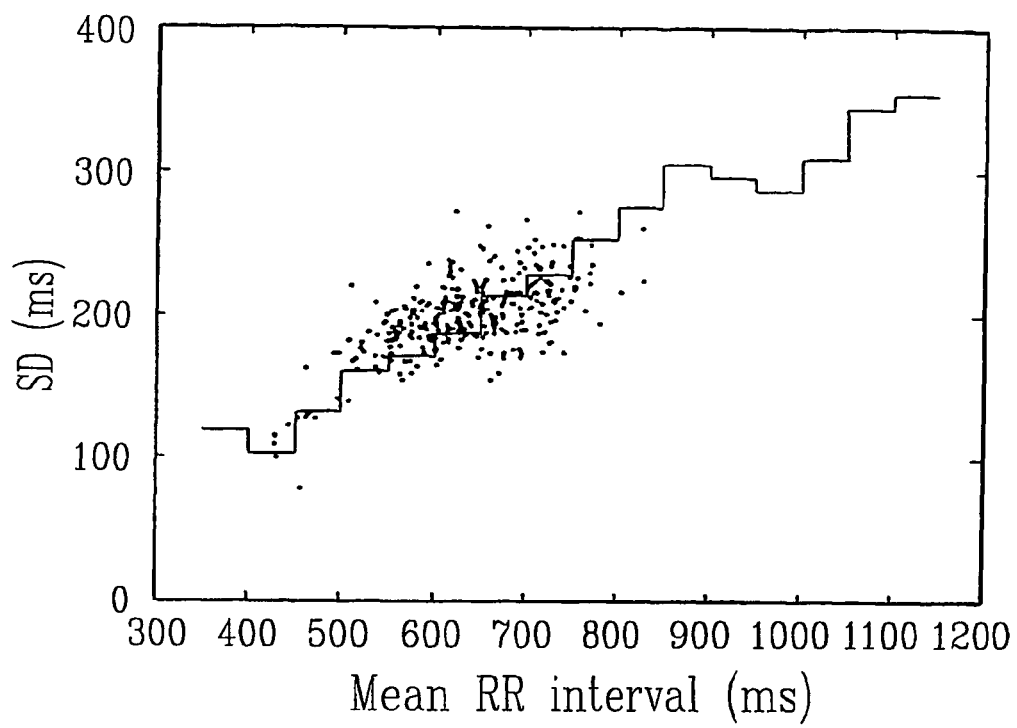
FIGS. 6a and 6b show an example of the standard deviation (FIG. 6a) and the skewness (FIG. 6b) of a test ΔRR probability density histogram. The line represents the standard deviation (FIG. 6a) and the skewness (FIG. 6b) of the standard ΔRR probability density histogram.
Figure 6B:
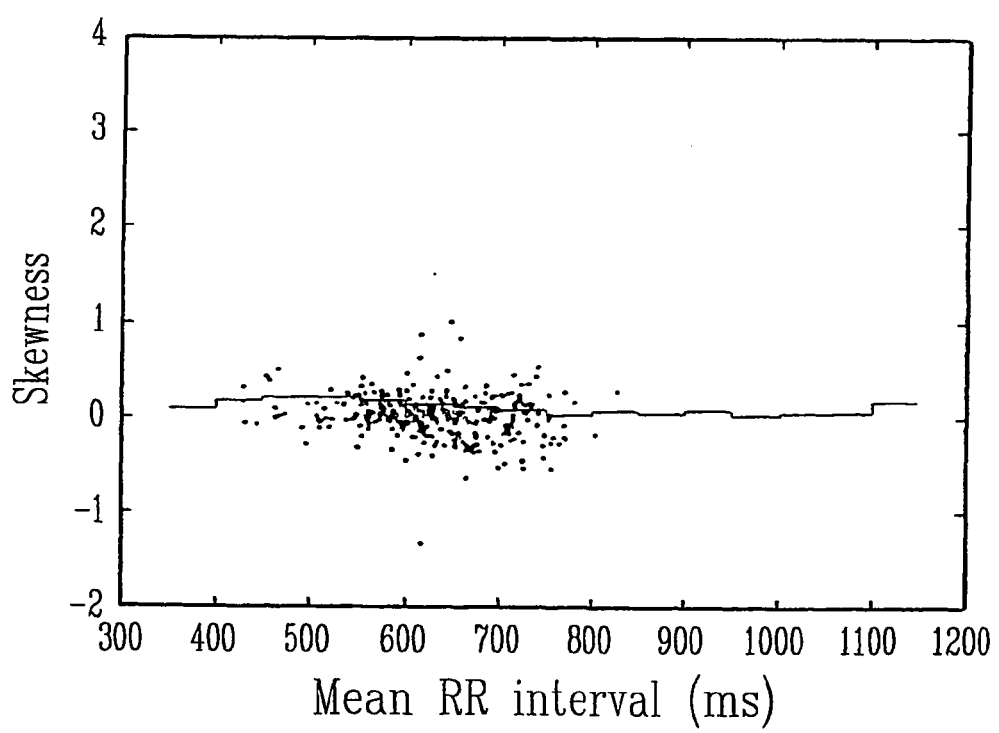

FIGS. 6a and 6b show a comparison of the ΔRR probability density histograms in terms of standard deviation and skewness. A small D defined above indicates that the standard deviation and the skewness of a test ΔRR probability density histogram are clustered around those of the standard ΔRR probability density histograms.

The results were assessed by four categories as followed: true positive (TP)—atrial fibrillation is classified as atrial fibrillation; true negative (TN)—non-atrial fibrillation is classified as non-atrial fibrillation; false negative (FN)—atrial fibrillation is classified as non-atrial fibrillation; false positive (FP)—non-atrial fibrillation is classified as atrial fibrillation. Sensitivity and specificity are defined by TP/(TP+FN) and TN/(TN+FP), respectively. The predictive value of a positive test (PV+) and the predictive value of a negative test (PV−) are defined by TP/(TP+FP) and TN/(TN+FN), respectively.

The receiver operating characteristic curve (ROC) gives the sensitivity and the specificity in the artrial fibrillation detection algorithm. Variation of the value of $P_c$ determines the ROC. FIG. 7 shows the ROC of the assessment of the KS test for the MIT-BIH atrial fibrillation/flutter database. Reducing $P_c$, the sensitivity increases and the specificity decreases. Assuming $P_c$=0.003944, the sensitivity is 96.5%, the specificity is 96.5%, the PV+ is 95.2% and PV− is 97.5%. $P_c$ is therefore a sensitivity-altering and specificity-altering parameter.

It will appear to those of ordinary skill in the art that the method of FIG. 2 and the system of FIG. 8 can be implemented through a properly programmed computer.

Although the present invention has been described hereinabove by way of a preferred embodiment thereof, this embodiment can be modified at will, within the scope of the appended claims, without departing from the spirit and nature of the subject invention.

What is claimed is:

1. A method for detecting cardiac arrhythmia comprising: detecting RR intervals of a patient, wherein each RR interval is an interval between two heart beats; constructing standard histograms of ΔRRs collected during cardiac arrhythmia of a plurality of subjects, wherein each ΔRR is a difference between two successive RR intervals; constructing test histograms of ΔRRs of the patient from the detected RR intervals of said patient, wherein the standard and test histograms are probability density histograms; calculating a mean value of a given number of successive RR intervals of the patient; choosing one of the standard probability density histograms in relation to said mean value, wherein choosing one of the standard probability density histograms comprises selecting the standard histogram corresponding to the range of RR intervals in which said mean value is located; and comparing said standard and test histograms to detect whether said patient suffers from cardiac arrhthymia.

2. A method for detecting cardiac arrhythmia as defined in claim 1, wherein said comparing of the standard and test histograms comprises adjusting a specificity-altering and sensitivity-altering parameter.

3. A method for detecting cardiac arrhythmia as defined in claim 2, wherein said comparing of the standard and test histograms comprises: calculating a standard cumulative probability distribution from said standard ΔRR probability density histograms; calculating a test cumulative probability distribution from said test ΔRR probability density histograms; computing a deviation between said standard and test distributions; and detecting cardiac arrhythmia when the computed deviation is higher than said specificity-altering and sensitivity-altering parameter.

4. A method for detecting cardiac arrhythmia as defined in claim 1, wherein said comparing of the standard and test histograms comprises calculating a standard cumulative probability distribution from said standard ΔRR probability density histograms, calculating a test cumulative probability distribution from said test ΔRR probability density histograms, and computing a deviation between said standard and test distributions.

5. A system for detecting cardiac arrhythmia comprising: a RR interval detecting monitor detecting RR intervals of a patient, wherein each RR interval is an interval between two heart beats; a standard ΔRR histogram storage unit in which are stored standard histograms of ΔRRs collected during cardiac arrhythmia of a plurality of subjects, wherein each ΔRR is a difference between two successive RR intervals; a test ΔRR histogram calculator supplied with the detected RR intervals from the monitor and constructing test histograms of said ΔRRs of said patient, wherein the standard and test histograms are probability density histograms; a calculator of a mean value of a given number of successive RR intervals of the patient; a selector of one of the standard probability density histograms in relation to said mean value, wherein the selector of one of the standard probability density histograms comprises means for selecting the standard histogram corresponding to the range of RR intervals in which said mean value is located; and a standard and test ΔRR histograms comparator supplied with said standard and test histograms, said comparator comprising a detector of cardiac arrhythmia of the patient responsive to the comparison of said standard and test histograms.

6. A system for detecting cardiac arrhythmia as defined in claim 5, wherein said standard and test ΔRR histograms comparator comprises an adjustable, specificity-altering and sensitivity-altering parameter.

7. A system for detecting cardiac arrhythmia as defined in claim 6, wherein the standard and test ΔRR histograms comparator comprises: a calculator of a standard cumulative probability distribution from said standard ΔRR probability density histograms; a calculator of a test cumulative probability distribution from said test ΔRR probability density histograms; a calculator of a deviation between said standard and test distributions; and a detector of a cardiac arrhythmia when the computed deviation is higher than said specificity-altering and sensitivity-altering parameter.

8. A system for detecting cardiac arrhythmia as defined in claim 5, wherein said standard and test ΔRR histograms comparator comprises a calculator of a standard cumulative probability distribution from said standard ΔRR probability density histograms, a calculator of a test cumulative probability distribution from said test ΔRR probability density histograms, and a calculator of a deviation between said standard and test distributions.

9. An apparatus, comprising: means for detecting RR intervals of a patient, wherein each RR interval is an interval between two heart beats; means for constructing standard histograms of ΔRRs collected during cardiac arrhythmia of a plurality of subjects, wherein each ΔRR is a difference between two successive RR intervals; means for constructing test histograms of ΔRRs of the patient from the detected RR intervals of said patient, wherein the standard and test histograms are probability density histograms; means for calculating a mean value of a given number of successive RR intervals of the patient and for choosing one of the standard probability density histograms in relation to said mean value, wherein the means for choosing one of the standard probability density histograms comprises means for selecting the standard histogram corresponding to the range of RR intervals in which said mean value is located; and means for comparing said standard and test histograms to detect whether said patient suffers from cardiac arrhthymia.

10. An apparatus according to claim 9, wherein said means for comparing of the standard and test histograms further comprises means for adjusting a specificity-altering and sensitivity-altering parameter.

11. An apparatus according to claim 9, wherein said means for comparing of the standard and test histograms further comprises means for calculating a standard cumulative probability distribution from said standard $\Delta$RR probability density histograms, calculating a test cumulative probability distribution from said test $\Delta$RR probability density histograms, and computing a deviation between said standard and test distributions.

12. An apparatus according to claim 11, wherein said means for comparing of the standard and test histograms further comprises:
   means for calculating a standard cumulative probability distribution from said standard $\Delta$RR probability density histograms;
   means for calculating a test cumulative probability distribution from said test $\Delta$RR probability density histograms;
   means for computing a deviation between said standard and test distributions; and
   means for detecting cardiac arrhythmia when the computed deviation is higher than said specificity-altering and sensitivity-altering parameter.

13. A computer readable medium encoded with executable instructions for performing a method, comprising:
   instructions for detecting RR intervals of a patient, wherein each RR interval is an interval between two heart beats;
   instructions for constructing standard histograms of $\Delta$RRs collected during cardiac arrhythmia of a plurality of subjects, wherein each $\Delta$RR is a difference between two successive RR intervals;
   instructions for constructing test histograms of $\Delta$RRs of the patient from the detected RR intervals of said patient, wherein the standard and test histograms are probability density histograms;
   instructions for calculating a mean value of a given number of successive RR intervals of the patient and for choosing one of the standard probability density histograms in relation to said mean value, wherein the instructions for choosing one of the standard probability density histograms comprises instructions for selecting the standard histogram corresponding to the range of RR intervals in which said mean value is located; and
   instructions for comparing said standard and test histograms to detect whether said patient suffers from cardiac arrhthymia.

14. A medium according to claim 13, wherein said instructions for comparing of the standard and test histograms further comprises instructions for adjusting a specificity-altering and sensitivity-altering parameter.

15. A medium according to claim 13, wherein said instructions for comparing of the standard and test histograms further comprises instructions for calculating a standard cumulative probability distribution from said standard $\Delta$RR probability density histograms, calculating a test cumulative probability distribution from said test $\Delta$RR probability density histograms, and computing a deviation between said standard and test distributions.

16. A medium according to claim 15, wherein said instructions for comparing of the standard and test histograms further comprises:
   instructions for calculating a standard cumulative probability distribution from said standard $\Delta$RR probability density histograms;
   instructions for calculating a test cumulative probability distribution from said test $\Delta$RR probability density histograms;
   instructions for computing a deviation between said standard and test distributions; and
   instructions for detecting cardiac arrhythmia when the computed deviation is higher than said specificity-altering and sensitivity-altering parameter.

* * * * *